(12) United States Patent
Celestini et al.

(10) Patent No.: US 11,045,400 B2
(45) Date of Patent: Jun. 29, 2021

(54) TOPICAL COSMETIC COMPOSITION FOR RESTRUCTURING AND PROTECTING HAIR AND SCALP, AND USES THEREOF

(71) Applicant: KEMON S.P.A., San Giustino (IT)

(72) Inventors: Sabrina Celestini, San Giustino (IT); Caterina Ghiara, San Giustino (IT); Giuliano Nocentini, San Giustino (IT); Federica Comanducci, San Giustino (IT)

(73) Assignee: KEMON S.P.A., San Giustino (IT)

( * ) Notice: Subject to any disclaimer, the term of this patent is extended or adjusted under 35 U.S.C. 154(b) by 0 days.

(21) Appl. No.: 16/320,331

(22) PCT Filed: Jul. 26, 2017

(86) PCT No.: PCT/IB2017/054529
§ 371 (c)(1),
(2) Date: Jan. 24, 2019

(87) PCT Pub. No.: WO2018/020431
PCT Pub. Date: Feb. 1, 2018

(65) Prior Publication Data
US 2019/0240126 A1    Aug. 8, 2019

(30) Foreign Application Priority Data
Jul. 27, 2016 (IT) .......... 102016000078766

(51) Int. Cl.
*A61K 8/31* (2006.01)
*A61K 8/36* (2006.01)
*A61K 8/365* (2006.01)
*A61K 8/44* (2006.01)
(Continued)

(52) U.S. Cl.
CPC .......... *A61K 8/31* (2013.01); *A61K 8/36* (2013.01); *A61K 8/365* (2013.01); *A61K 8/44* (2013.01); *A61K 8/4913* (2013.01); *A61Q 5/002* (2013.01); *A61K 2800/95* (2013.01)

(58) Field of Classification Search
None
See application file for complete search history.

(56) References Cited

U.S. PATENT DOCUMENTS 5,332,581 A * 7/1994 Yoshihara ............ A61K 8/34
424/401
7,879,910 B1 * 2/2011 Marini ............ A61K 31/19
514/573
(Continued)

FOREIGN PATENT DOCUMENTS

DE    102008048438 A1    3/2010
DE    102012215046 A1    5/2013
(Continued)

OTHER PUBLICATIONS

Derwent English abstract for JP2003-12470. (Year: 2003).*
(Continued)

*Primary Examiner* — Sin J Lee
(74) *Attorney, Agent, or Firm* — King & Schickli, PLLC

(57) ABSTRACT

A topical cosmetic composition is described for restructuring and protecting hair and scalp, as well as products for hair and scalp care involving the same.

11 Claims, 1 Drawing Sheet

(A)

(B)

(C)

(51) Int. Cl.
*A61K 8/49* (2006.01)
*A61Q 5/00* (2006.01)

(56) References Cited

U.S. PATENT DOCUMENTS

| | | | | |
|---|---|---|---|---|
| 2006/0024257 | A1* | 2/2006 | Chang | A61K 8/02 424/70.2 |
| 2008/0089855 | A1* | 4/2008 | Walter | A61K 8/8147 424/70.11 |
| 2013/0211136 | A1* | 8/2013 | Tg | C12N 9/1092 562/508 |
| 2014/0296366 | A1* | 10/2014 | Spevacek | C08J 7/16 522/184 |
| 2015/0037270 | A1 | 2/2015 | Pressly et al. | |
| 2015/0328102 | A1* | 11/2015 | Pressly | A45D 7/04 424/70.1 |
| 2016/0120783 | A1* | 5/2016 | Horie | A61Q 5/12 424/62 |

FOREIGN PATENT DOCUMENTS

| | | |
|---|---|---|
| JP | H0291015 A | 3/1990 |
| JP | 2003-12470 * | 1/2003 |
| WO | WO9937148 A1 | 7/1999 |

OTHER PUBLICATIONS

Machine-assisted English translation for JP2003-12470. (Year: 2003).*
Derwent English abstract for DE 10 2012 215 046 A1. (Year: 2013).*
Machine-assisted English translation for DE 10 2012 215 046 A1. (Year: 2013).*
Database GNPD Mintel XP-002769556 (Zenagen, "Treatment for Men" (Jun. 1, 2016)) (Year: 2016).*
"Proline", Truth in Aging, an internet article obtained from the website https://www.truthinaging.com/ingredients/proline (dated Jul. 7, 2009) (Year: 2009).*
Database GNPD Mintel; Feb. 1, 2005; Da-Chuan Co. "Essential Treatment Oils for Hair". XP002769553.
Database GNPD Mintel; Dec. 1, 2005; Kang Fa Wei; "Milk Essence Hair Care". XP002769554.
Database GNPD Mintel; Jul. 1, 2015; Laboratoires Phytosolba; "Protective Oil". XP002769555.
Chiu, C.H., et al., Abstract of "A Review: Hair Health, Concerns of Shampoo Ingredients and Scalp Nourishing Treatments"; Curr. Pharm. Biotechnol. 2015; 16(12); accessed on PubMed.
Colomer, A., et al., Abstract of "Cationic surfactants derived from lysine; effects of their structure and charge type on antimicrobial and hemolytic activities", J. Med. Chem,. Feb. 24, 2011; 54(4); accessed on PubMed.

* cited by examiner

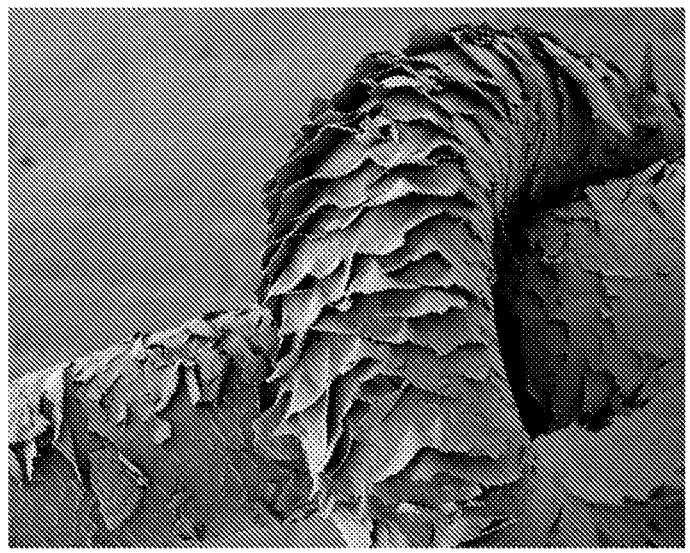
(A)
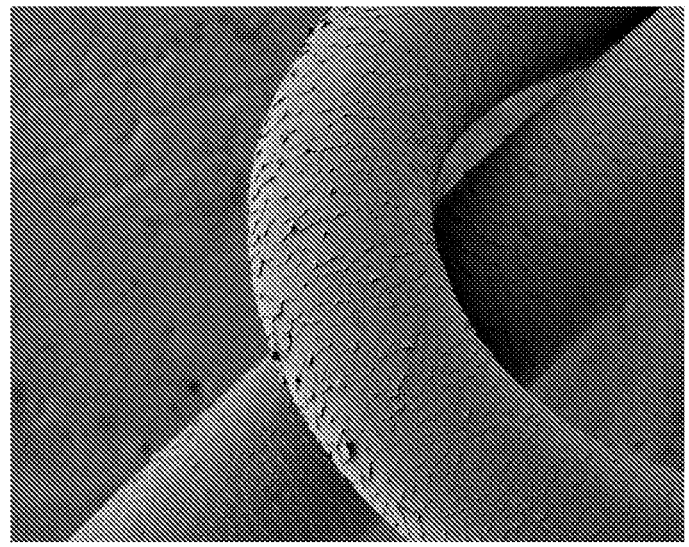
(B)
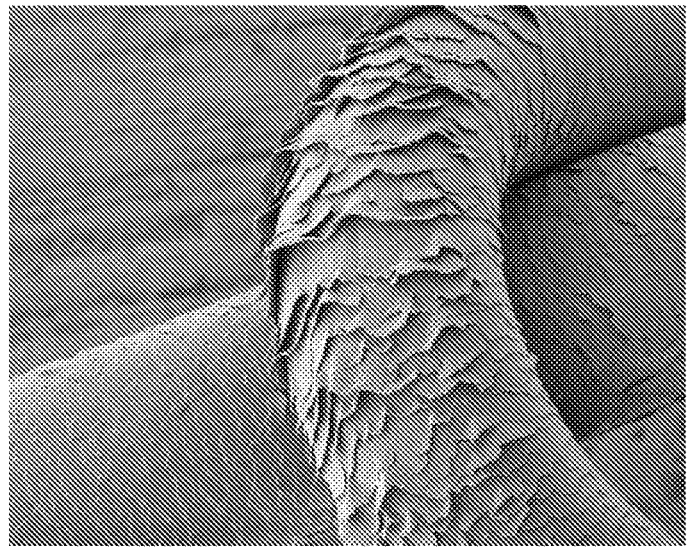
(C)

TOPICAL COSMETIC COMPOSITION FOR RESTRUCTURING AND PROTECTING HAIR AND SCALP, AND USES THEREOF

FIELD OF THE INVENTION

The present invention relates to a topical cosmetic composition for restructuring and protecting hair and scalp, as well as products for hair and scalp care involving the same.

BACKGROUND ART

The hair has a very complex composition that includes, in addition to water, also keratin, lipids, minerals, and pigments.

Keratin is a protein located in the hair cuticle. It consists of eighteen amino acids, among which the most important are cysteine, cystine, serine, glutamic acid, glycine, threonine, arginine, valine, leucine, and isoleucine.

Alpha keratin, fibrous and low-sulphur content, is the type of keratin present in the highest amount in hair. It has a molecular weight of about 45,000 Da and is insoluble in water. Keratin can be deformed with water vapor (the so-called "hair set").

Macromolecules are very large helix-shaped molecules; the latter form bundles of three helices, holding together by sulphur bonds —S—S—, thus giving a protofibrilla. Two other types of bonds contribute to this cohesion among the various helices of keratin proteins given by the disulphide bridges, though to a lesser extent and with less stable bonds:
- salt bonds,
- hydrogen bonds The water breaks hydrogen bonds in a reversible manner and this facilitates the setting of wet hair. When the water evaporates, the hydrogen bonds form again in new positions while maintaining the hair set.

Under particular conditions of high acidity (pH 1 to 2), both hydrogen and salt bonds are broken, but disulphide bonds may still hold together protein chains.

However, even from a weakly alkaline pH (8.5), some of disulphide bridges are broken. Repeated washings with weakly alkaline shampoos as well as repeated colouring or bleaching treatments damage the hair resulting in the breaking of an ever-increasing number of disulphide bonds. This determines the scaling of the cuticle and the outer surface of the capillary fibre, thus leaving the wet hair full of knots and impossible to comb. This can cause the formation of split ends. After drying, hair look arid, frizzy, unruly, and rough at touch. Rough and damaged hair interacts with the light in an uneven manner, thus making the capillary fibre opaque, dull and strongly electrified after combing.

Disulphide bonds can also be broken by heat treatment or by treatment with reducing agents.

The current formulations and methods for hair waving and straightening make use of reducing agents such as thioglycolic acid and its salts (especially ammonium) to break the cystine disulphide bonds present in the hair.

After the disulphide bonds have been broken and the hair is held in position for obtaining the final style (smooth or curly), these disulphide bonds are then rebuilt. Oxidation for the restoration of reduced bonds could be obtained by simple exposure to atmospheric oxygen (this process is very slow and is never used in practice); in fact, hydrogen peroxide is generally used.

However, newly formed disulphide bonds are subjected to stress to keep the new setting given to the capillary fibre, so, in the long run, the new bonds break more easily causing hair return to the starting state. In addition, the use of peroxides in the hairstyle can result in hair damage, artificial colour removal, and/or frizzy effect. Moreover, some latent free tiols may remain non-neutralized in hair after the oxidative treatment.

Treatment with oxidants used in hair waving and straightening processes is highlighted by the following reaction:

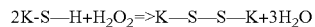

wherein K denotes the hair keratin.

However, if two groups 2K-S—H are not present in the reaction, it is believed that the following reaction typical of damaged hair occurs:

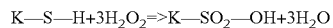

In order to remedy these problems, various approaches have been developed which include applying post-shampoo conditioners both rinse off and leave on. Generally, after the conditioner application, lipid protection is restored, especially on the hair areas where the cuticle is damaged. However, excessive amount of conditioner or an over-conditioning product will make hair more heavy and prone to soiling, thus making necessary more frequent shampoo washings. Generally, the conditioners do not bind free hair thiols.

The use of cationic polymers for coacervate formation is known to provide the hair with conditioning benefits. Commonly used cationic deposition polymers include natural polymers, such as guar gum polymers, which have been modified by cationic substitutions. The selection of a guar cationic polymer, with adequate charge density and molecular weight, results in a sufficient deposition of conditioning agents when incorporated in a shampoo. However, a relatively high level of this guar cationic polymer should generally be deposited on the hair to be effective, this results in an increase in the cost of formulation; Moreover, shampoos based on guar cationic polymers are typically recommended on wet hair, but they are not able to make your hair straight to the touch once it's dry. It should also be noted that these balms do not bind free hair thiols.

It is therefore necessary to formulate hair treatments that can give the best conditioning benefits to the capillary fibre. In particular, it is felt the need to provide arid hair with prolonged hydration to make them soft and detangleable and treatments that repair and strengthen damaged hair, by restoring strong bonds deteriorated after the application of cosmetic services, especially those based on reducing or oxidizing agents.

It is therefore an object of the present invention to provide more advanced compositions and innovative methods for using the same, with the aim of repairing and/or reinforcing damaged hair.

More specifically, an object of the present invention is to provide compositions and methods for using the same to repair and/or strengthen hair after washing or after a reduction or oxidation treatment.

SUMMARY OF THE INVENTION

This object has been achieved through the cosmetic use of an acyclic terpene as an active agent in restructuring and protecting hair and scalp, in topical cosmetic compositions, as claimed in claim 1.

In another aspect, the present invention also relates to a topical cosmetic composition comprising an active component in restructuring and protecting hair and scalp, said active component comprising at least one acyclic terpene.

In a further aspect, the present invention also relates to a product for hair and scalp care comprising said topical cosmetic composition.

In another aspect, the present invention also relates to the cosmetic use of said topical cosmetic composition for restructuring and protecting hair and scalp.

BRIEF DESCRIPTION OF THE DRAWINGS

The characteristics and the advantages of the present invention will become apparent from the following detailed description, from the working examples provided for illustrative and non-limiting purposes, and from the annexed FIG. 1 wherein:

FIG. 1A shows the surface of destructured hair before any restructuring treatment, FIG. 1B shows the surface of hair treated with the composition of Example 6, and FIG. 1C shows the surface of hair treated with placebo.

DETAILED DESCRIPTION OF THE INVENTION

The invention therefore relates to the cosmetic use of an acyclic terpene as an active agent in restructuring and protecting hair and scalp, in topical cosmetic compositions.

Particularly, with "topical cosmetic composition" it is meant a cosmetic composition to be topically applied and for external use.

It has surprisingly found that, as it will be clear from the Examples provided herein below, said acyclic terpene advantageously allows to protect the hair and scalp structure, while effectively reconstituting and repairing the same, wherever damaged.

In fact, damaged hair and scalp show on their surface free —SH groups, deriving from the breaking of disulphide bonds. Said groups are among the most powerful nucleophilic entities with which said at least one acyclic terpene interacts, through the so-called thiol-ene click reaction.

Particularly, said acyclic terpene is a C10-C40 hydrocarbon acyclic terpene.

Suitable C10-C40 hydrocarbon acyclic terpenes are myrcene, ocimene, farnesene, squalene, and lycopene. It is believed that each hydrocarbon acyclic terpene molecule advantageously reacts with tiol groups bridging them together.

Preferably said acyclic terpene is squalene.

In another aspect, the present invention also relates to a cosmetic composition comprising 1) an active component in restructuring and protecting hair and scalp, said active component comprising at least one acyclic terpene.

Particularly, said acyclic terpene is a C10-C40 hydrocarbon acyclic terpene.

Suitable C10-C40 hydrocarbon acyclic terpenes are myrcene, ocimene, farnesene, squalene, phytoene, phytofluene, farnesol, and lycopene.

Preferably said acyclic terpene is squalene, phytoene, or phytofluene.

More preferably, said at least one acyclic terpene is squalene.

In preferred embodiments, said active component is in a concentration up to 75 wt % on the composition weight.

Preferably, in the topical cosmetic composition of the invention, said active component further comprises at least one Michael acceptor compound.

Michael's reaction is a nucleophilic addition reaction, involving a donor species (powerful nucleophile) and an accepting species (e.g. an unsaturated alpha-beta carbonyl compound). As mentioned, damaged hair and scalp have free —SH groups on their surface, resulting from the breaking of the disulphide bridges. Said groups are among the most powerful nucleophiles, thus acting as Michael donors.

With the term "Michael acceptor", it is meant a cosmetically acceptable unsaturated alpha-beta carbonyl compound, including, for the purposes of the present invention, also its salts, all polymorphic forms, both amorphous and crystalline, and co-crystalline, as well as the anhydrous, hydrate and solvate forms.

Preferably, said Michael acceptor compound has formula (I):

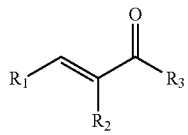

(I)

wherein $R_1$, $R_2$ and $R_3$ are, independently of one another, hydrogen, or a linear, branched, or cyclic, saturated or unsaturated, aliphatic or aromatic moiety selected from C1-C10 alkyl, C1-C10 substituted alkyl, C2-C10 alkenyl, C2-C10 substituted alkenyl, C4-C10 dienyl, C4-C10 substituted dienyl, C2-C10 alkynyl, C2-C10 substituted alkynyl, phenyl, substituted phenyl, aryl, substituted aryl, heteroaryl, substituted heteroaryl, halogen, hydroxy, C1-C10 alkoxy, C1-C6 substituted alkoxy, phenoxy, substituted phenoxy, aroxy, substituted aroxy, C1-C10 alkylthio, C1-C10 substituted alkylthio, phenylthio, substituted phenylthio, arylthio, substituted arylthio, cyano, isocyano, substituted isocyano, carbonyl, C1-C6 substituted carbonyl, carboxy, C1-C6 substituted carboxy, amino, C1-C6 substituted amino, amido, C1-C6 substituted amido, sulfonyl, C1-C6 substituted sulfonyl, sulphonic acid, phosphoryl, C1-C6 substituted phosphoryl, phosphonyl, C1-C6 substituted phosphonyl, polyaryl, substituted polyaryl, C3-C20 cycloalkyl, C3-C20 substituted cycloalkyl, C3-C20 heterocycloalkyl, C3-C20 substituted heterocycloalkyl, C2-C10 cycloalkenyl, C2-C10 substituted cycloalkenyl, C4-C10 cyclodienyl, C4-C10 substituted cyclodienyl, or amino acid, or $R_1$ and $R_2$ form a 5-8 membered ring or a substituted 5-8 membered ring.

With "substituted", it is meant bound to at least a halogen, hydroxy, C1-C4 alkyl, carboxy, or combinations thereof.

In preferred embodiments, in said at least one Michael acceptor compound of formula (I), when $R_1$ and $R_2$ are hydrogen, $R_3$ is not hydroxy, C1-C10 alkoxy, amino.

In other preferred embodiments, in said at least one Michael acceptor compound of formula (I), when $R_1$ is hydrogen and $R_2$ is hydroxy, $R_3$ is not carboxy or C1-C6 substituted carboxy.

In preferred embodiments, the composition of the invention comprises at least one Michael acceptor of formula (I), wherein:

$R_1$ is a linear moiety selected from those listed above, $R_2$ is hydrogen and $R_3$ is hydroxy, or $R_1$ and $R_2$ form a substituted 5-7 membered ring, and $R_3$ is hydroxy, or $R_1$ is hydrogen, $R_3$ is hydroxy, and $R_2$ is C3-C20 cycloalkyl, C3-C20 substituted cycloalkyl, C3-C20 heterocycloalkyl, C3-C20 substituted heterocycloalkyl, C2-C10 cycloalkenyl, C2-C10 substituted cycloalkenyl, C4-C10 cyclodienyl, or C4-C10 substituted cyclodienyl, or $R_1$ is phenyl, substituted phenyl, aryl, substituted aryl, heteroaryl, or substituted heteroaryl, $R_2$ is hydrogen, and $R_3$ is phenyl, substituted phenyl, aryl, substituted aryl, heteroaryl, or substituted heteroaryl.

Preferably, the composition of the invention comprises at least one Michael acceptor of formula (I) wherein $R_1$ is a linear C2-C10 alkenyl, $R_2$ is hydrogen and $R_3$ is hydroxy, or at least one Michael acceptor of formula (I) wherein $R_1$ and $R_2$ form a 6-membered ring substituted with at least one hydroxy, and $R_3$ is hydroxy.

In some particularly preferred embodiments, said at least one Michael acceptor of formula (I) is sorbic acid or a salt thereof.

In other particularly preferred embodiments, said at least one Michael acceptor of formula (I) is octatrienoic acid or a salt thereof.

In other particularly preferred embodiments, said at least one Michael acceptor of formula (I) is shikimic acid or a salt thereof.

Preferably, the composition of the invention comprises at least one Michael acceptor of formula (I) wherein $R_1$ is hydrogen, $R_3$ is hydroxy, and $R_2$ is C2-C10 cycloalkenyl, C2-C10 substituted cycloalkenyl, C4-C10 cyclodienyl, or C4-C10 substituted cyclodienyl.

In some particularly preferred embodiments, said at least one Michael acceptor of formula (I) is chorismic acid or a salt thereof.

Preferably, the composition of the invention comprises at least one Michael acceptor of formula (I) wherein $R_1$ is phenyl, substituted phenyl, aryl, substituted aryl, heteroaryl, or substituted heteroaryl, $R_2$ is hydrogen, and $R_3$ is phenyl, substituted phenyl, aryl, substituted aryl, heteroaryl, or substituted heteroaryl.

In some particularly preferred embodiments, said at least one Michael acceptor of formula (I) is chalcone.

Alternatively, said Michael acceptor is selected from flavones, isoflavones, coumarin, flavonols, and mixtures thereof.

In other preferred embodiments, the composition of the invention comprises at least two Michael acceptors.

In more preferred embodiments, the composition of the invention comprises at least one Michael acceptor of formula (I) wherein $R_1$ and $R_3$ are, independently of each other, a linear moiety selected from those listed above, and $R_2$ is hydrogen, and at least one Michael acceptor of formula (I) wherein $R_1$ and $R_2$ form a substituted 5-7 membered ring, and $R_3$ is hydroxy.

In other embodiments, the composition of the invention comprises at least one Michael acceptor of formula (I) wherein $R_1$ is a linear moiety selected from those listed above, $R_2$ is hydrogen and $R_3$ is hydroxy, and at least one Michael acceptor of formula (I) wherein $R_1$ and $R_2$ form a substituted 5-7 membered ring, and $R_3$ is hydroxy.

Preferably, the composition of the invention comprises at least one Michael acceptor of formula (I) wherein $R_1$ is a linear C2-C6 alkenyl, $R_2$ is hydrogen and $R_3$ is hydroxy, and at least one Michael acceptor of formula (I) wherein $R_1$ and $R_2$ form a 6-membered ring substituted with at least one hydroxy, and $R_3$ is hydroxy.

In particularly preferred embodiments, the composition of the invention comprises at least one Michael acceptor of formula (I) wherein $R_1$ is a linear C3-C6 alkenyl, $R_2$ is hydrogen and $R_3$ is hydroxy, and at least one Michael acceptor of formula (I) wherein $R_1$ and $R_2$ form a 6-membered ring substituted with at least one hydroxy, and $R_3$ is hydroxy.

Particularly preferred are those embodiments wherein the composition of the invention comprises sorbic acid and shikimic acid.

Preferably, the topical cosmetic composition of the invention further comprises 2) at least one catalyst, said catalyst comprising proline, zinc pyrrolidone carboxylate, or a mixture thereof. The catalyst serves to accelerate the reaction of the composition on hair and scalp, therefore with the addition of a catalyst, the effects of the composition can be observed at much shorter times.

In preferred embodiments, said at least one catalyst is in a concentration up to 60 wt % on the composition weight.

Preferably, the topical cosmetic composition of the invention further comprises 3) at least one linker. With the term "linker", it is meant an atom or a moiety comprising at least one functional group, which may be used to bind said at least one Michael acceptor compound or said at least one acyclic terpene or both, to the thiol groups of hair.

In preferred embodiments, said at least one linker is in concentration up to 35 wt % on the composition weight.

Suitable linkers comprise oxygen, sulphur, carbon, boron, nitrogen, alkoxy, alkyl, alkenyl, cycloalkyl, cycloalkenyl, aryl, heterocycloalkyl, heteroaryl, ether, amine and combinations thereof. Preferably, said linker is a linker comprising at least one amino moiety. More preferably, said linker is a linker comprising two amino moieties.

In some embodiments, said linker is selected from lysine, arginine, cysteine, selenocysteine, glutamine, asparagine, ethylenediamine, propane-1,3-diamine, hexamethylene diamine, ornithine, salts thereof, and mixtures thereof.

In preferred embodiments, said amino linker is lysine or salt thereof.

In some embodiments, the topical cosmetic composition of the invention comprises:
1) an active component comprising a mixture of at least one acyclic terpene and at least one Michael acceptor compound, and
3) at least one linker.

Preferably, said active component is in a concentration up to 85 wt % on the weight of components 1)-3).

With "weight of components 1)-3)", it is meant the sum of the weights of components 1) and 3).

Preferably, said at least one acyclic terpene is in a concentration up to 55 wt % on the weight of components 1)-3).

Preferably, said active component comprises a mixture of at least one acyclic terpene and at least one Michael acceptor compound, and said at least one Michael acceptor compound is in a concentration up to 70 wt % on the weight of components 1)-3).

Preferred are those embodiments wherein the topical cosmetic composition of the invention comprises:
1) 30-95 wt % of an active component comprising a mixture of at least one acyclic terpene and at least one Michael acceptor compound, and
3) 5-30 wt % of at least one linker, on the weight of components 1)-3).

In particularly preferred embodiments, the topical cosmetic composition of the invention comprises:
1) an active component comprising at least one acyclic terpene or a mixture of at least one acyclic terpene and at least one Michael acceptor compound,
2) at least one catalyst, said catalyst comprising proline, zinc pyrrolidone carboxylate, or a mixture thereof, and
3) at least one linker.

In fact, as said, the presence of one linker accelerates the reaction of the composition on hair and scalp.

Preferably, said active component is in a concentration up to 75 wt % on the weight of components 1)-3).

With "weight of components 1)-3)", it is meant the sum of the weights of components 1) to 3).

Preferably, said at least one acyclic terpene is in a concentration up to 45 wt % on the weight of components 1)-3).

Preferably, said active component comprises a mixture of at least one acyclic terpene and at least one Michael acceptor compound, and said at least one Michael acceptor compound is in a concentration up to 60 wt % on the weight of components 1)-3).

In particularly preferred embodiments, said active component comprises a mixture of at least one acyclic terpene and at least two Michael acceptor compounds.

Particularly preferred are those embodiments wherein said at least two Michael acceptor compounds are at least one Michael acceptor compound of formula (I) wherein $R_1$ is a linear moiety selected from those listed above, $R_2$ is hydrogen and $R_3$ is hydroxy, and at least one Michael acceptor of formula (I) wherein $R_1$ and $R_2$ form a substituted 5-7 membered ring, and $R_3$ is hydroxy. More preferably, said at least two Michael acceptor compounds are at least one Michael acceptor of formula (I) wherein $R_1$ is a linear C2-C6 alkenyl, $R_2$ is hydrogen and $R_3$ is hydroxy, and at least one Michael acceptor of formula (I) wherein $R_1$ and $R_2$ form a 6-membered ring substituted with at least one hydroxy, and $R_3$ is hydroxy.

Even more preferred are those embodiments wherein said at least two Michael acceptor compounds are sorbic acid and shikimic acid.

In preferred embodiments, said active component consists of at least one acyclic terpene or a mixture of at least one acyclic terpene and at least one Michael acceptor compound.

Preferably, said at least one catalyst is in a concentration up to 60 wt % on the weight of components 1)-3).

Preferably, said at least one linker is in a concentration up to 35 wt % on the weight of components 1)-3).

Preferred are those embodiments, wherein the topical cosmetic composition of the invention comprises:
1) 30-70 wt % of at least one acyclic terpene,
2) 25-60 wt % of at least one catalyst, said catalyst comprising proline, zinc pyrrolidone carboxylate, or a mixture thereof, and
3) 5-30 wt % of at least one linker, on the weight of components 1)-3).

Particularly preferred are those embodiments wherein said active component comprises a mixture of at least one acyclic terpene and at least one Michael acceptor compound. As will be seen from the following working examples, these embodiments have shown a surprisingly synergistic effect, as the simultaneous presence of at least one acyclic terpene and at least one Michael acceptor compound has allowed to obtain a very reduced residue of broken hair at the end of treatment, as compared to untreated hair and hair treated in the presence of only one of the two active components, each one being singularly very effective anyway.

Preferably, said active component is a mixture of at least one acyclic terpene and at least one Michael acceptor compound, wherein said at least one Michael acceptor compound is in a quantity higher than said at least one acyclic terpene.

Particularly, are even more preferred those embodiments wherein the topical cosmetic composition of the invention comprises:
1) 40-70 wt % of a mixture of at least one acyclic terpene and at least one Michael acceptor compound,
2) 20-40 wt % of at least one catalyst, said catalyst comprising proline, zinc pyrrolidone carboxylate, or a mixture thereof, and
3) 10-20 wt % of at least one linker, on the weight of components 1)-3).

The topical cosmetic composition of the invention preferably has a pH of 2 to 10.

Preferably, the topical cosmetic composition of the invention comprises up to 50 wt % of components 1) to 3), on the composition weight.

The topical cosmetic composition of the invention may optionally also comprise one or more cosmetically acceptable excipients.

Preferably, the topical cosmetic composition of the invention comprises up to 75 wt % of cosmetically acceptable excipients, on the composition weight.

Cosmetically acceptable excipients comprise water, preservatives, antioxidants, chelating agents, sunscreening agents, vitamins, silanes, silanols, hair dye agents, keratin softeners, proteins, diluents, amino acids, natural plant extracts, wetting agents, fragrances, perfumes, oils, emollients, lubricants, butters, permeation enhancers, thickeners, viscosity modifiers, polymers, resins, hair binders, film forming agents, surfactants, detergents, emulsifiers, dulling agents, propellants, conditioning agents, liquid vehicles, salts, pH regulators, neutralizing agents, buffers, antistatic agents, anti-frizzing agents, anti-dandruff agents, absorbent agents, and mixtures thereof.

Suitable keratin softeners comprise allantoin, glycols and polyalcohols, such as glycerol, erythritol, sorbitol, pyrrolidone carboxylic acid and salts thereof, betaine, and combinations thereof.

Surfactants can be amphoteric, anionic or cationic.

Suitable surfactants are 3-aminosulfonic acid, almond amide, almond amidopropyl betaine, almond amidopropylamine oxide, aluminium lanolate, aminoethyl sulfate, aminopropyl lauryl glutamine, ammonium C12-15 alkyl sulfate, ammonium C12-15 pareth sulfate, ammonium C12-C16 alkyl sulfate, ammonium C9-10 perfluoroalkylsulphonate, ammonium caprileth sulfate, ammonium capryleth-3 sulphate, ammonium monoglyceride sulphate, ammonium sulphate, ammonium isothionate, ammonium cocoyl sarcosinate, ammonium cumene sulfonate, ammonium dimethicone copolyol sulphate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxinol-4 sulphate, ammonium oleate, ammonium polyacrylate, ammonium stearate, ammonium tallate, ammonium xylene sulfonate, AMP-isostearoyl gelatine/keratin amino acids/lysine hydroxypropyltriammonium chloride, AMP-isostearoyl collagen hydrolysed, PEG-6 esters of apricot kernel oil, apricot amine, apricot amidopropyl betaine, arachideth-20, avocadamide, avocadamido propyl betaine, babassuamide, babassuamidopropyl betaine, babas suamidopropylamine oxide, behenalconium chloride, behenamide, behenamidopropyl betaine, behenamine oxide, sodium laureth sulfate, sodium lauryl sulphate, or combinations thereof.

Suitable anionic surfactants include those containing carboxylated, sulfonated and sulphated ions. Examples of anionic surfactants include sodium, potassium, ammonium of long chain alkyl sulfonates and alkyl aryl sulfonates, such as sodium dodecylbenzene sulfonate; dialkyl sodium sulfosuccinates, such as sodium dodecylbenzene sulfonate; sodium dialkyl sulfosuccinates, such as sodium bis-(2-ethylthioxyl)sulfosuccinate; and alkyl sulphates such as sodium lauryl sulfate. Cationic surfactants include quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, acylated sorbitan, acylated sucrose, laurate PEG-150, monolaurate PEG-400, monolaurate polyoxyethylene, polysorbates, polyoxyethylene octylphenylether, PEG-1000 cetyl ether, polyoxyethylene tridecyl ether, polypropylene glycol butyl ether, Poloxamer 401, and stearoyl monoisopropanolamide. Examples of amphoteric surfactants include sodium N-dodecyl-beta-alanine, sodium N-lauryl-p-iminodipropionate, myristoamphoacetate, lauryl betaine and lauryl sulfobetaine.

The topical cosmetic composition of the invention optionally and preferably comprises up to 40 wt % of surfactants on the composition weight.

Suitable emollients comprise silicones, such as dimethicone, cyclomethicone, dimethicone copolyol or a mixture of cyclopentasiloxane and dimethicone/vinyl dimethicone crosslinked polymer, cyclopentasiloxane polysilicone; polyols such as sorbitol, glycerol, propylene glycol, ethylene glycol, polyethylene glycol, caprylyl glycol, polypropylene glycol, 1,3-butanediol, hexylene glycol, isoprene glycol, xylitol, ethylhexyl palmitate; a triglyceride, such as caprylic/capric triglyceride; and fatty acid esters, such as cetearyl isononanoate or cetyl palmitate.

The topical cosmetic composition of the invention optionally and preferably comprises up to 10 wt % of emollients on the composition weight.

Suitable emulsifiers comprise copolymers of an unsaturated ester and monomeric styrene sulfonate, cetearyl alcohol, glyceryl ester, polyoxyethylene glycol ethers of cetearyl alcohol, stearic acid, polysorbate-20, ceteareth-20, lecithin, stearate glycol, polysorbate-60, or polysorbate-80, and combinations thereof.

The topical cosmetic composition of the invention optionally and preferably comprises up to 10 wt % of emulsifiers on the composition weight.

Suitable preservatives comprise glycerine-containing compounds (for example, glycerine or ethylhexyl glycerol or phenoxyethanol), benzyl alcohol, parabens (methylparaben, ethylparaben, propylparaben, butylparaben, isobutylparabene, etc.), sodium benzoate, Leuconostoc/Radish root ferment filtrate, EDTA, potassium sorbate, grapefruit seed extract, salicylic acid, DMDM hydantoin, imidazolidinyl urea, diazolidinyl urea, methylisothiazolinone, sodium dehydroacetate, dehydroacetic acid, Quaternium-15, stearalconium chloride, zinc pyrithione, sodium metabisulphite, 2-bromo-2-nitropropane, chlorhexidine digluconate, polyaminopropyl biguanide, benzalkonium chloride, sodium sulphite, sodium salicylate, citric acid, neem oil, essential oils, lactic acid, vitamin E, and combinations thereof.

The topical cosmetic composition of the invention optionally and preferably comprises up to 5 wt % of preservatives on the composition weight.

In some embodiments, the topical cosmetic composition of the invention does not comprise preservatives.

Suitable conditioning agents include silicones (for example silica Quaternium-8), panthenol, hydrolysed wheat and/or soy proteins, hydrolysed pea protein, amino acids (e.g., wheat amino acids), rice bran wax, mango seed oil, grape seed oil, jojoba seed oil, sweet almond oil, aloe leaf extract, aloe barbadensis leaf juice, phytantriol, retinyl palmitate, behentrimonium methosulfate, cyclopentasiloxane, Quaternium-91, stearamidopropyl dimethylamine, and combinations thereof.

The topical cosmetic composition of the invention optionally and preferably comprises up to 5 wt % of conditioning agents on the composition weight.

As for diluents, water is the preferred diluent, but alcohols such as ethyl alcohol and isopropyl alcohol are also suitable.

Suitable viscosity modifiers are viscous liquids such as polyethylene glycol, semisynthetic polymers, for example semi-synthetic cellulose derivatives, synthetic polymers such as carbomers, polyoxamers and polyethyleneimines, natural polymers such as acacia, tragacanth, alginates (e.g., sodium alginate), carrageenan, vegetable gums, such as xanthan gum, vaseline, waxes, bentonite, colloidal silicon dioxide, and microcrystalline cellulose, salts such as sodium chloride, and combinations thereof. Suitable antioxidants comprise tocopherols, BHT, ascorbic acid, *Camellia sinensis* leaf extract, *Selaginella lepidophylla* extract, ascorbyl palmitate, magnesium ascorbyl phosphate, carotenoids, resveratrol, triethyl citrate, arbutin, cogic acid, tetrahexyldecyl ascorbate, superoxide dismutase, zinc, sodium metabisulphite, ubiquinone, and combinations thereof.

Suitable dulling agents comprise glycol distearate and ethoxylated fatty alcohols.

In other embodiments, the topical cosmetic composition of the invention consists essentially of:
1) an active component comprising at least one acyclic terpene or a mixture of at least one acyclic terpene and at least one Michael acceptor compound,
2) at least one catalyst, said catalyst comprising proline, zinc pyrrolidone carboxylate, or a mixture thereof, and
3) at least one linker.

With the term "consists essentially of", it is understood that the above-mentioned ingredients (1) to (3) are the only active ingredients in the protection and repair of hair and scalp, being the remaining ingredients only excipients and bulking agents. It should be understood that all the aspects identified as preferred and advantageous for the composition and its components are to be likewise preferred and advantageous also for these embodiments.

In further embodiments, the topical cosmetic composition of the invention consists of:
1) an active component comprising at least one acyclic terpene or a mixture of at least one acyclic terpene and at least one Michael acceptor compound,
2) at least one catalyst, said catalyst comprising proline, zinc pyrrolidone carboxylate, or a mixture thereof, and
3) at least one linker, and
one or more cosmetically acceptable excipients.

It should be understood that all the aspects identified as preferred and advantageous for the composition and its components are to be likewise preferred and advantageous also for these embodiments.

In another aspect, the present invention also relates to a product for hair and scalp care comprising said topical cosmetic composition.

Preferably, said product for hair and scalp care comprises up to 50 wt % of topical cosmetic composition of the invention on the product weight.

This product for hair and scalp care can be a lotion, milk, mousse, gel, cream, shampoo, conditioner, compress, mask, oil, emulsion o/w and emulsion w/o, silicone emulsion, multiple emulsion, microemulsion, hydroalcoholic solution, hydroglyceric solution, ointment, lipogel, paste, stick, cream-gel, or combination thereof. This product can be packaged in a pressurized device.

The topical cosmetic composition of the invention can thus be used as an active ingredient for the restructuring and protecting hair and scalp in dedicated products. Thus, in a further aspect, the present invention also relates to the cosmetic use of said topical cosmetic composition for restructuring and protecting hair and scalp.

In particular, said composition can be applied on both wet and dry hair and can be left in place for up to 120 minutes, preferably up to 60 minutes. After the placing, the composition of the invention can be rinsed away with water, with or without shampoo.

Given the beneficial effects of the use of the composition on the scalp, said composition may advantageously be used also for the restructuring and protecting skin and skin annexes.

As will be seen from the following examples, preferred embodiments of the topical cosmetic composition of the invention, wherein said active component is a mixture of at least one Michael acceptor compound and at least one acyclic terpene, showed also a surprising synergistic effect, as the simultaneous presence of at least one Michael acceptor compound and at least one acyclic terpene has allowed to obtain a very reduced residue of broken hair at the end of treatment, as compared to untreated hair and hair treated in the presence of only one of the two active components, each one being singularly very effective anyway. Therefore, an advantageous hair protective effect has also been achieved, as well as a restructuring effect even after different hair treatments such as bleaching, dyeing, permanent, and straightening.

The composition of the present invention can be prepared by methods known in the art, for example by direct mixing the ingredients.

It should be understood that all possible combinations of the preferred aspects of the composition, products for hair and scalp care comprising said topical cosmetic composition, as well as the uses as reported above, are hereby described and likewise preferred.

It should to be understood that all aspects identified as preferred and advantageous for the composition and its components are likewise preferred and advantageous also for the preparation and uses of the composition itself, and for products for hair and scalp care comprising said topical cosmetic composition.

Below are working examples of the present invention provided for illustrative purposes.

EXAMPLES

Example 1

The following composition (100 g) has been prepared:

| Ingredients | grams |
| --- | --- |
| Sorbic acid | 13.3 |
| Shikimic acid | 33.3 |
| Lysine | 17.8 |
| Proline | 17.8 |
| Zinc PCA | 17.8 |

Example 2

The following composition (100 g) has been prepared:

| Ingredients | grams |
| --- | --- |
| Squalene | 38.5 |
| Lysine | 20.5 |
| Proline | 20.5 |
| Zinc PCA | 20.5 |

Example 3

The following composition (100 g) has been prepared:

| Ingredients | grams |
| --- | --- |
| Sorbic acid | 10.0 |
| Shikimic acid | 25.0 |
| Squalene | 25.0 |
| Lysine | 13.4 |
| Proline | 13.3 |
| Zinc PCA | 13.3 |

Example 4

The following composition (100 g) has been prepared:

| Ingredients | grams |
| --- | --- |
| Sorbic acid | 3.7 |
| Shikimic acid | 9.0 |
| Squalene | 9.0 |
| Lysine | 4.9 |
| Proline | 4.9 |
| Zinc PCA | 4.9 |
| Excipients: | 63.6 |
| allantoin | |
| Polyquaternium-80 | |
| hydrolysed pea protein | |
| *Selaginella Lepidophylla* extract | |
| Leuconostoc/Radish root ferment filtrate | |

Example 5

In order to demonstrate the efficacy of the compositions of the invention, as well as the synergistic effect of preferred embodiments, the following compositions were prepared and tested:
1) placebo
2) composition with sorbic acid and shikimic acid (Example 1)
3) composition with squalene (Example 2)
4) composition with sorbic acid and shikimic acid+squalene (Example 3)

"Placebo" means a base of water and excipients only, such as solubilizer, preservative and pH regulator, as follows:

| Ingredients | grams |
| --- | --- |
| Water | q.s. a 100 |
| Phenoxyethanol | 1.0 |
| Lactic acid | 1.0 |
| Polysorbate 20 | 10 |

The tests were conducted with the aim of verifying both the restructuring and protecting function during chemical hair treatment.

Parameters Evaluated:

Evaluation of residue: treated and dried hair locks are weighed with an analytical balance. The residue is calculated as the percentage of broken hair weight after combing cycles, on the initial weight of the hair locks.

Sensory Evaluation:

The sensory evaluation of the hair locks is performed visually by 3 experienced judges.

| Evaluating scale used: | Score |
| --- | --- |
| frizzy, dull, and rough at touch hair locks | 4 |
| quite frizzy, quite dull, and quite rough at touch hair locks | 3 |
| slightly frizzy, slightly dull, and slightly rough at touch hair locks | 2 |
| non-frizzy, non-dull, and non-rough at touch hair locks | 1 |

A) Restructuring Protocol:

Untreated brown-based hair locks were prepared, each having a weight of 6-7 grams, and subjected to 3 bleaching cycles with a decolouring agent and oxygen 40 vol.

Subsequently, the hair locks were subjected to a treatment with the respective composition, left in place for 45 minutes, under heating source, washed with a shampoo and dried.

Each hair lock was subjected to 10 combing cycles at the end of which the broken hair residue was evaluated and the hair lock was analysed from the sensory point of view:

| Test | % loss on residue | sensory evaluation |
| --- | --- | --- |
| placebo | 0.6197 | 4 |
| sorbic acid and shikimic acid | 0.0783 | 2.5 |
| squalene | 0.0847 | 2.5 |
| sorbic acid and shikimic acid + squalene | 0.0162 | 1 |

B) Protecting Protocol Over Bleaching:

Untreated brown-based hair locks were prepared, and subjected to 3 consecutive bleaching cycles with a decolouring agent and oxygen 40 vol. and the respective composition. Each bleaching cycle included 45 minutes of placing on a plate. Then, the hair locks were washed with a shampoo and dried.

Each hair lock was subjected to 10 combing cycles at the end of which the broken hair residue was evaluated and the hair lock was analysed from the sensory point of view:

| Test | % loss on residue | sensory evaluation |
| --- | --- | --- |
| placebo | 0.7420 | 4 |
| sorbic acid and shikimic acid | 0.0597 | 1.5 |
| squalene | 0.0631 | 1.5 |
| sorbic acid and shikimic acid + squalene | 0.0204 | 1 |

C) Protecting Protocol Over Dyeing:

Untreated brown-based hair locks were prepared, each having a weight of 6-7 grams, and subjected to a dyeing treatment with a dye and oxygen 20 vol. in suitable ratios, and the respective composition. 30 minutes of placing on a plate were included. Then, the hair locks were washed with a shampoo and dried.

Each hair lock was subjected to 10 combing cycles at the end of which the broken hair residue was evaluated and the hair lock was analysed from the sensory and visual point of view:

| Test | % loss on residue | sensory evaluation |
| --- | --- | --- |
| placebo | 0.5964 | 2.5 |
| sorbic acid and shikimic acid | 0.0642 | 1.5 |
| squalene | 0.0697 | 1.5 |
| sorbic acid and shikimic acid + squalene | 0.0258 | 1 |

D) Protecting Protocol Over Permanent:

Untreated brown-based hair locks were prepared, each having a weight of 6-7 grams. A waving product was applied to the same, and then wrapped on hair rollers. Hair locks were left in place for 20 minutes on a plate. Then, the hair locks were washed with a shampoo and dried.

Each hair lock was subjected to 10 combing cycles at the end of which the broken hair residue was evaluated and the hair lock was analysed from the sensory and visual point of view:

| Test | % loss on residue | sensory evaluation |
| --- | --- | --- |
| placebo | 0.6154 | 3 |
| sorbic acid and shikimic acid | 0.0943 | 1.6 |
| squalene | 0.0832 | 1.6 |
| sorbic acid and shikimic acid + squalene | 0.0351 | 1 |

E) Protecting Protocol Over Straightening:

Untreated brown-based hair locks were prepared, each having a weight of 6-7 grams. A straightening product was applied to the same (10 g). Hair locks were left in place for 25 minutes on a plate. Then, the hair locks were washed with a shampoo and dried. 14 passages between plates were performed.

Each hair lock was subjected to 10 combing cycles at the end of which the broken hair residue was evaluated and the hair lock was analysed from the sensory and visual point of view:

| Test | % loss on residue | sensory evaluation |
| --- | --- | --- |
| placebo | 0.5936 | 2.5 |
| sorbic acid and shikimic acid | 0.0686 | 1.6 |
| squalene | 0.0714 | 1.6 |
| sorbic acid and shikimic acid + squalene | 0.0285 | 1 |

F) Beauty Amplifier Protocol:

Untreated brown-based hair locks were prepared, each having a weight of 6-7 grams. Hair locks were washed with a shampoo, towel-dried, and then treated with the respective composition, leaving in place for 15 minutes on a plate. Then, the hair locks were washed with a shampoo and dried.

Each hair lock was subjected to 10 combing cycles at the end of which the broken hair residue was evaluated and the hair lock was analysed from the sensory and visual point of view:

| Test | % loss on residue | sensory evaluation |
| --- | --- | --- |
| Placebo | 0.1610 | 2 |
| sorbic acid and shikimic acid | 0.0327 | 1 |
| squalene | 0.0351 | 1 |
| sorbic acid and shikimic acid + squalene | 0.0108 | 1 |

As can be seen from the results shown in the above tables, the protective and repairing efficacy of the compositions of the invention is clear, while being even more clear and surprising in the compositions comprising at least one Michael acceptor compound, and at least one acyclic terpene. In fact, it should also be considered that the compositions of Example 3 comprise at least one Michael acceptor compound and at least one acyclic terpene in amounts lower than those of the corresponding components of Examples 1 and 2, thus the synergistic effect observed for Example 3 is even more significant and relevant.

Example 6

The following compositions (100 g) have been prepared:

| Ingredients | Placebo grams | Example 6 grams |
| --- | --- | --- |
| Potassium sorbate | 0 | 0.45 |
| Shikimic acid | 0 | 1 |
| Squalene | 0 | 1.5 |
| Lysine hydrochloride | 0 | 0.72 |
| Proline | 0 | 0.72 |
| Zinc PCA | 0 | 0.19 |
| Water | q.s. a 100 | q.s. a 100 |
| Excipients: | 12.1 | 12.29 |
| allantoin | | |
| Polisorbate-20 | | |
| phenoxyethanol | | |
| lactic acid | | |
| xanthan gum | | |

Untreated brown-based hair locks were prepared, each having a weight of 6-7 grams, and subjected to 3 bleaching cycles with a decolouring agent and oxygen 40 vol.

Subsequently, the hair locks were subjected to a treatment with the respective composition, left in place for 45 minutes, under heating source, washed with a shampoo and dried.

Each hair lock was subjected to 10 combing cycles at the end of which the broken hair residue was evaluated, and the hair lock was analysed from the sensory point of view, and by Scanning Electron Microscope (SEM) analysis:

A) Analysis of the Residue of Broken Hair

| | % loss on residue | sensory evaluation |
| --- | --- | --- |
| Placebo | 0.7276 | 4 |
| Example 6 | 0.0689 | 1 |

B) Analysis at Scanning Electron Microscope (SEM):

The microscopic hair structure was qualitatively analysed by using an Electronic Scanning Microscope (SEM). Five sections of each hair were selected from each hair lock. The hair was placed on a support and fixed with a small amount of adhesive. The acquisition was made with the following settings:

EHT=20.00 kV (extra high tension)

Signal A=QBSD (Quadrant Back Scattering Detector)

WD=7.0-7.5 mm (working distance)

Magnification=1.00KX

The resulting images are reported in FIG. 1, where:

FIG. 1A shows the hair surface before any treatment,

FIG. 1B shows the hair surface treated with the composition of Example 6, and

FIG. 1C shows the hair surface treated with placebo.

The remarkable result obtained by applying the composition of the invention was evident, since the hair surface appeared clearly more compact and uniform.

Example 7

The following composition (100 g) has been prepared:

| Ingredients | grams |
| --- | --- |
| Potassium sorbate | 0.8 |
| Shikimic acid | 1.5 |
| Squalene | 1.5 |
| Lysine hydrochloride | 0.8 |
| Water | q.s. a 100 |
| Excipients: | 11.6 |
| Polisorbate-20 | |
| phenoxyethanol | |
| xanthan gum | |

Untreated brown-based hair locks were prepared, each having a weight of 6-7 grams, and subjected to 3 bleaching cycles with a decolouring agent and oxygen 40 vol.

Subsequently, the hair locks were subjected to a treatment with the above composition, and, in a first case, left in place for 45 minutes, whereas, in a second case, for 4 hours, under heating source, washed with a shampoo and dried.

Each hair lock was subjected to 10 combing cycles at the end of which the broken hair residue was evaluated.

Analysis of the Residue of Broken Hair:

|  | % loss on residue |
| --- | --- |
| after 45 minutes | 0.5586 |
| after 4 hours | 0.0989 |

This test showed that the presence of catalysts is not essential to obtain the desired result, but allows to accelerate its achievement.

Examples 8-11

The following compositions (100 g) have been prepared:

| Ingredients | Example 8 grams | Example 9 grams | Example 10 grams | Example 11 grams |
| --- | --- | --- | --- | --- |
| Potassium sorbate | // | 0.8 | // | 0.26 |
| Shikimic acid | // | // | 1.5 | 0.5 |
| Potassium octatrienoate | 2 | // | // | 0.65 |
| Squalene | 1.5 | 1.5 | 1.5 | 1.5 |
| Lysine hydrochloride | 0.8 | 0.8 | 0.8 | 0.8 |
| Proline | 0.8 | 0.8 | 0.8 | 0.8 |
| Zinc PCA | 0.8 | 0.8 | 0.8 | 0.8 |
| Water | q.s. a 100 | q.s. a 100 | q.s. a 100 | q.s. a 100 |
| Excipients: allantoin Polisorbate-20 Phenoxyethanol Xanthan gum | 12.1 | 12.1 | 12.1 | 12.1 |

Untreated brown-based hair locks were prepared, each having a weight of 6-7 grams, and subjected to 3 bleaching cycles with a decolouring agent and oxygen 40 vol.

Subsequently, the hair locks were subjected to a treatment with the respective composition, left in place for 45 minutes, under heating source, washed with a shampoo and dried.

Each hair lock was subjected to 10 combing cycles at the end of which the broken hair residue was evaluated.

Analysis of the Residue of Broken Hair:

|  | % loss on residue |
| --- | --- |
| Placebo (v. Example 6) | 0.85240 |
| Example 8 | 0.07763 |
| Example 9 | 0.06340 |
| Example 10 | 0.09178 |
| Example 11 | 0.04593 |

Examples 12-19

The following compositions (100 g) have been prepared:

| Ingredients | Ex. 12 grams | Ex. 13 grams | Ex. 14 grams | Ex. 15 grams | Ex. 16 grams | Ex. 17 grams | Ex. 18 grams | Ex. 19 grams |
| --- | --- | --- | --- | --- | --- | --- | --- | --- |
| Potassium sorbate | — | 0.45 | 0.45 | 0.5 | — | — | 0.2 | 0.4 |
| Shikimic acid | — | 1 | 0.05 | — | 0.8 | — | 0.2 | 0.2 |
| Potassium octatrienoate | 1.2 | — | — | — | — | 2.0 | — | — |
| Squalene | 1.5 | — | — | 1.5 | 0.25 | — | — | 0.5 |
| Phytoene | — | 1.5 | — | — | — | — | 1.5 | — |
| Phytofluene | — | — | 1.5 | — | — | 1.5 | — | — |
| Lysine hydrochloride | 0.8 | — | — | — | — | — | 0.8 | — |
| Arginine | — | 0.5 | 0.5 | — | — | — | — | 0.5 |
| Hexamethylenediamine | — | — | — | 0.5 | 0.5 | 0.5 | — | — |
| Proline | 0.8 | 0.8 | 0.8 | 0.8 | 0.8 | 0.8 | 0.8 | 0.8 |
| Zinc PCA | 0.8 | 0.8 | 0.8 | 0.8 | 0.8 | 0.8 | 0.8 | 0.8 |
| Water | q.s. 100 | q.s. 100 | q.s. 100 | q.s. 100 | q.s. 100 | q.s. 100 | q.s. 100 | q.s. 100 |
| Excipients: allantoin Polisorbate-20 phenoxyethanol xanthan gum | 12.1 | 12.1 | 12.1 | 12.1 | 12.1 | 12.1 | 12.1 | 12.1 |

Untreated brown-based hair locks were prepared, each having a weight of 6-7 grams, and subjected to 3 bleaching cycles with a decolouring agent and oxygen 40 vol. Subsequently, the hair locks were subjected to a treatment with the respective composition, left in place for 45 minutes, under heating source, washed with a shampoo and dried. Each hair lock was subjected to 10 combing cycles at the end of which the broken hair residue was evaluated.

Analysis of the Residue of Broken Hair:

|  | % loss on residue |
|---|---|
| Placebo (v. Example 6) | 0.82320 |
| Example 12 | 0.07128 |
| Example 13 | 0.09652 |
| Example 14 | 0.09164 |
| Example 15 | 0.07633 |
| Example 16 | 0.07165 |
| Example 17 | 0.08450 |
| Example 18 | 0.08085 |
| Example 19 | 0.08297 |

Examples 20-27

The following compositions (100 g) have been prepared:

| Ingredients | Ex. 20 grams | Ex. 21 grams | Ex. 22 grams | Ex. 23 grams | Ex. 24 grams | Ex. 25 grams | Ex. 26 grams | Ex. 27 grams |
|---|---|---|---|---|---|---|---|---|
| Potassium sorbate | 0.8 | 0.45 | 0.45 | 0.05 | 0.8 | 0.4 | 0.08 | 0.4 |
| Shikimic acid | 1.5 | 1 | 0.05 | 0.05 | 0.25 | 0.075 | 0.015 | 0.15 |
| Squalene | 1.5 | 1.5 | 1 | 0.1 | 0.25 | 0.075 | 0.005 | 0.5 |
| Lysine hydrochloride | 0.8 | 0.72 | 0.1 | 0.001 | 0.13 | 0.04 | 0.008 | 0.05 |
| Proline | 0.8 | 0.72 | 0.1 | 0.001 | 0.13 | 0.04 | 0.008 | 0.05 |
| Zinc PCA | 0.8 | 0.19 | 0.1 | 0.001 | 0.13 | 0.04 | 0.008 | 0.05 |
| Water | q.s. 100 | q.s. 100 | q.s. 100 | q.s. 100 | q.s. 100 | q.s. 100 | q.s. 100 | q.s. 100 |
| Excipients: allantoin Polisorbate-20 phenoxyethanol xanthan gum | 12.1 | 12.1 | 12.1 | 12.1 | 12.1 | 12.1 | 12.1 | 12.1 |

Untreated brown-based hair locks were prepared, and subjected to 3 consecutive bleaching cycles with a decolouring agent and oxygen 40 vol. and the respective composition. Each bleaching cycle included 45 minutes of placing on a plate. Then, the hair locks were washed with a shampoo and dried.

Each hair lock was subjected to 10 combing cycles at the end of which the broken hair residue was evaluated.

|  | % loss on residue |
|---|---|
| Placebo (v. Example 6) | 0.82320 |
| Example 20 | 0.07128 |
| Example 21 | 0.06921 |
| Example 22 | 0.07266 |
| Example 23 | 0.08432 |
| Example 24 | 0.05892 |
| Example 25 | 0.08365 |
| Example 26 | 0.06149 |
| Example 27 | 0.07381 |

Example 28

The following compositions (100 g) have been prepared:

| Ingredients | Example 28 grams | Placebo grams |
|---|---|---|
| Potassium sorbate | 0.080 | 0 |
| Shikimic acid | 0.015 | 0 |
| Squalene | 0.005 | 0 |
| Lysine hydrochloride | 0.008 | 0 |
| Proline | 0.008 | 0 |
| Zinc PCA | 0.008 | 0 |
| Water | q.s. a 100 | q.s. a 100 |
| Excipients: allantoin polyquaternium-10 coco betaine sodium laureth sulfate PEG-18 glyceryl oleate/cocoate perfume PEG-40 hydrogenated castor oil ethoxydiglycol phenoxyethanol DMDM hydantoin disodium EDTA citric acid PEG-120 methyl glucose dioleate | 42.85 | 42.85 |

Example 29

The following composition (100 g) has been prepared:

| Ingredients | grams |
|---|---|
| Potassium sorbate | 0.40 |
| Shikimic acid | 0.075 |
| Squalene | 0.075 |
| Lysine hydrochloride | 0.04 |
| Proline | 0.04 |
| Zinc PCA | 0.04 |
| Water | q.s. a 100 |
| Excipients: allantoin behentrimonium chloride cetrimonium chloride glycerine isopropyl alcohol perfume phenoxyethanol DMDM hydantoin disodium EDTA citric acid | 15.7 |

Example 30

Evaluation of the Effectiveness of Compositions of the Previous Examples

In order to evaluate the effectiveness in improving the structure and mechanical properties of the hair, an ex vivo test was performed on hair locks (n. 10) of natural hair subjected to a de-structuring cycle; all the hair locks were subjected to a first treatment (professional treatment), after which 5 hair locks were treated with the home-use product according to the present invention and 5 hair locks were subjected to washing only with placebo shampoo, i.e. a shampoo comprising the composition "Placebo" reported in Example 28.

1) Professional Treatment According to the Invention:

Wash with a shampoo comprising the composition of Example 28 (1 gram per hair lock); apply a serum comprising the composition of Example 20 (3 grams per hair lock): 15 min of placing time, while having covered hair with a shower cap (on a plate heated at 35° C. to simulate body temperature); apply a mask comprising the composition of Example 29 (1.5 gram per hair lock) overlaying the serum for 5 minutes (on a plate heated at 35° C. to simulate body temperature); rinse abundantly; towel-dry the hair lock; dry.

2) Home Treatment According to the Invention:

Wash with a shampoo comprising the composition of Example 28 (1 gram per hair lock); apply a mask comprising the composition of Example 29 for 5 minutes (3 gram per hair lock) (on a plate heated at 35° C. to simulate body temperature); rinse abundantly; towel-dry the hair lock; dry; repeat for 4 more times.

3) Home Treatment with Placebo:

Wash with placebo shampoo (1 gram for hair lock); rinse abundantly; towel-dry the hair lock; dry; repeat for 4 more times.

Procedure Followed:

As said, the hair locks have been de-structured by means of a 40-volume bleach treatment. After the bleaching procedure, the hair locks were washed with neutral shampoo, dried with a hairdryer and then subjected to professional treatment 1). Subsequently, 5 hair locks were subjected to home treatment 2) and dried with a hairdryer (4 cycles repeated), and 5 hair locks were subjected to home treatment 3) with placebo shampoo and dried with a hairdryer (4 cycles repeated).

Tests Performed

Hydration

The measurement of the hydration degree of the hair takes place indirectly by using the Tewameter® TM 300 (Courage+Khazaka, electronic GmbH) instrument. The physical basis of measurement is the Law of Diffusion discovered by Adolf Fick in 1855:

$$dm/dt = -D*A*dp/dx$$

The law of diffusion dm/dt denotes the water mass per cm² transported over a period of time. It is proportional to area A and change of concentration over space, i.e. dp/dx. D is the water vapor diffusion coefficient in the air. This law is valid only for a homogeneous diffusion area, which is formed approximately by a cylinder. The resulting density gradient is measured indirectly by two pairs of sensors (temperature and relative humidity) and is analysed by a microprocessor. The probe measurement head is a shallow cylinder (diameter 10 mm and length 20 mm) in order to minimize the influences due to air turbulence within the probe. Water loss is measured continuously for one hour. At the end of the measurement, the area under the curd is calculated. A calibration curve is drawn by known amounts of water (0, 10, 50, 100, 200, 400, 600 microlitres).

Brightness of Hair

The "gloss" parameter is measured by using the spectrophotometer/colorimeter CM-700d (Konica Minolta). The "gloss" value represents the specular component of the reflected light and is correlated with the perception of brightness/luminosity. The instrument evaluates the colour in accordance with the international standard developed by the International Commission on Illumination (CIE). The brightness is measured in three points of the hair lock (high, medium, low) and then the average is calculated on the three measurements.

Hair Elasticity

Hair elasticity (maximum elongation before breakage) is evaluated by dynamometer (Tensolab 2512A, Mesdan Lab) in accordance with the UNI EN ISO 5079: 1998 method. Hair elasticity is calculated as the force required to break the single hair.

Hair Diameter

The diameter of the hair stalk is evaluated by image analysis.

Clinical Evaluation

The experimenter evaluates the hair volume and consistency at any experimental time by using a clinical judgment scale (see Table 1 and 2).

TABLE 1

| Clinical evaluation of hair volume score | |
|---|---|
| Unchanged hair lock surface | 1 |
| Slight increase of the hair lock surface | 2 |
| Evident increase of the hair lock surface | 3 |

TABLE 2

| Clinical evaluation of hair consistency score | |
|---|---|
| Dull and arid hair, damaged throughout its length | 1 |
| Slightly arid, slightly dull hair, slightly damaged stalk, arid ends | 2 |
| Acceptably bright, non-arid hair, slightly damaged ends | 3 |
| Soft, bright, non-arid hair | 4 |

RESULTS AND CONCLUSIONS

| | Treatment 1) | Treatments 1) + 2) | Treatments 1) + 3) |
|---|---|---|---|
| Hydration (increase vs. post-destructuring) | +62.5% | +70.1% | +29.9% |
| Brightness (increase vs. post-destructuring) | +12.7% | +35.9% | +6.0% |
| Diameter (increase vs. post-destructuring) | +8.9% | +10.9% | +0.5% |

|  | Destructuring | Treatment 1) | Treatments 1) + 2) | Treatments 1) + 3) |
| --- | --- | --- | --- | --- |
| Hair consistency° | 1.0 | 2.5 | 4.0 | 1.4 |
| Hair volume°° | — | 1.5 | 1.2 | 1.0 |

°average score based on a reference clinical scale of 1 (dull and arid hair, damaged throughout its length) to 4 (Soft, bright, non-arid hair)
°°average score based on a reference clinical scale (1: unchanged hair lock surface, 2: slight increase of the hair lock surface, 3: evident increase of the hair lock surface).

As demonstrated by the data shown in the tables above, the professional treatment 1) was effective in improving the evaluated parameters. In particular, the values of hydration, brightness, elasticity, thickness and general appearance of previously destructured hair are increased.

In addition, these results are further improved or maintained with home treatment 2) and are also statistically significant.

Home treatment 3) with placebo shampoo conversely shows a worsening of values obtained with professional treatment 1), thereby highlighting the repair action of the comprehensive treatment with the products of the present invention.

The invention claimed is:

1. A topical cosmetic composition comprising
    30-95% by weight of an active component in restructuring and protecting hair and scalp, by restoring disulphide bonds which are broken on damaged hair and scalp, said active component comprising a mixture of at least one acyclic terpene and at least two Michael acceptor compounds, and
    5-30% by weight of at least one linker, based on the weight of said active component and said at least one linker;
    wherein said at least two Michael acceptor compounds are sorbic acid and shikimic acid; and
    wherein said at least one linker comprises an amino moiety, and is selected from the group consisting of lysine, arginine, cysteine, selenocysteine, glutamine, asparagine, ethylenediamine, propane-1,3-diamine, hexamethylene diamine, ornithine, salts thereof, and mixtures thereof; and wherein said at least one acyclic terpene is selected from the group consisting of myrcene, ocimene, farnesene, squalene, phytoene, phytofluene, farnesol and lycopene.

2. The topical cosmetic composition of claim 1, wherein said at least one acyclic terpene is squalene.

3. The topical cosmetic composition of claim 1, further comprising at least one catalyst, and comprising up to 50% by weight of said active component, said at least one catalyst, and said at least one linker, based on the composition weight.

4. The topical cosmetic composition of claim 3, wherein said at least one catalyst comprises proline, zinc pyrrolidone carboxylate, or a mixture thereof.

5. The topical cosmetic composition of claim 3, wherein said at least one acyclic terpene is in a concentration up to 45% by weight on the weight of said active component, said at least one catalyst, and said at least one linker.

6. The topical cosmetic composition of claim 3, wherein said at least two Michael acceptor compound are in a concentration up to 60% by weight on the weight of said active component, said at least one catalyst, and said at least one linker.

7. The topical cosmetic composition of claim 3, wherein said at least one catalyst is in a concentration up to 60% by weight on the weight of said active component, said at least one catalyst, and said at least one linker.

8. The topical cosmetic composition of claim 3, wherein said at least one linker is in a concentration up to 35% by weight on the weight of said active component, said at least one catalyst, and said at least one linker.

9. The topical cosmetic composition of claim 1, comprising
    40-70% by weight of said mixture of at least one acyclic terpene and at least two Michael acceptor compounds,
    20-40% by weight of at least one catalyst, said at least one catalyst comprising proline, zinc pyrrolidone carboxylate, or a mixture thereof, and
    10-20% by weight of said at least one linker, based on the weight of said active component, said at least one catalyst, and said at least one linker.

10. A product for hair and scalp care comprising the topical cosmetic composition of claim 1, said product being lotion, milk, mousse, gel, cream, shampoo, conditioner, compress, mask, oil, emulsion o/w, emulsion w/o, silicone emulsion, multiple emulsion, microemulsion, hydro-alcoholic solution, hydro-glyceric solution, ointment, lipogel, paste, stick, cream-gel, or a combination thereof.

11. A cosmetic method for restructuring and protecting hair and scalp, said method comprising applying to hair or scalp the topical cosmetic composition of claim 1.

* * * * *

UNITED STATES PATENT AND TRADEMARK OFFICE
CERTIFICATE OF CORRECTION

PATENT NO. : 11,045,400 B2  
APPLICATION NO. : 16/320331  
DATED : June 29, 2021  
INVENTOR(S) : Celestini et al.

Page 1 of 1

It is certified that error appears in the above-identified patent and that said Letters Patent is hereby corrected as shown below:

In the Claims

Column 24, Claim 6, Line 15 – please replace "compound is" with ---compounds are---

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*